United States Patent [19]
Howell et al.

[11] Patent Number: 5,348,742
[45] Date of Patent: Sep. 20, 1994

[54] **ANTI-PATHOGENIC BACTERIAL STRAINS OF *PSEUDOMONAS FLUORESCENS***

[75] Inventors: Charles R. Howell, Bryan, Tex.; J. Ole Becker, Inzlingen, Fed. Rep. of Germany; Stephen T. Lam, Raleigh; James M. Ligon, Cary, both of N.C.

[73] Assignees: Ciba-Geigy Corporation, Ardsley, N.Y.; The United States of America as represented by the United States Department of Agriculture, Washington, D.C.

[21] Appl. No.: 46,464

[22] Filed: Apr. 13, 1993

Related U.S. Application Data

[63] Continuation of Ser. No. 705,424, May 24, 1991, abandoned.

[51] Int. Cl.$^5$ .................. A01N 63/00; C12N 1/20; C12N 1/00; C05F 11/08
[52] U.S. Cl. .................. 424/93.47; 424/405; 424/93.3; 435/252.1; 435/252.34; 435/252.4; 435/822; 435/876; 435/253.3; 71/6; 504/101; 504/117
[58] Field of Search ............ 435/252.1, 252.34, 252.4, 435/822, 876; 424/93 N, 405; 71/3, 6, 65

[56] References Cited

U.S. PATENT DOCUMENTS

| | | | |
|---|---|---|---|
| 4,456,684 | 6/1984 | Weller et al. | 435/34 |
| 4,636,520 | 1/1987 | Umio et al. | 514/399 |
| 4,647,533 | 3/1987 | Weller et al. | 435/29 |
| 4,695,455 | 9/1987 | Barnes et al. | 424/93 |
| 4,900,348 | 3/1990 | Hoitink | 435/252.1 |
| 4,996,157 | 3/1991 | Smith et al. | 435/254 |
| 5,068,105 | 11/1991 | Lewis et al. | 435/254 |
| 5,102,898 | 4/1992 | Hsu | 514/375 |

FOREIGN PATENT DOCUMENTS

| | | |
|---|---|---|
| 0414404 | 2/1991 | European Pat. Off. |
| 0471564 | 2/1992 | European Pat. Off. |
| WO9105475 | 5/1991 | PCT Int'l Appl. |
| 9208355 | 5/1992 | PCT Int'l Appl. |

OTHER PUBLICATIONS

Weller et al., *Phytopathology*, 73:463–469 (1983).
Howell et al., *Phytopathology*, 69: 480–482 (1979).
Loper, *Phytopathology*, 78:166–171 (1988).
Thomashow et al., *J. Bacteriology*, 170:3499–3508 (1988).
Scher et al., *Phytopathology*, 70:412–417 (1980).
Kloepper et al., *Phytopathology*, 71:1020–1024 (1981).
Howell et al., *Can. J. Microbiol.*, 29:321–324 (1983).
Howell et al., *Phytopathology*, 70:712–715 (1980).
Baker et al., *Biological Control of Plant Pathogens*, pp. 61–106 (American Phytopathological Society, St. Paul, Minn., 1982).
James et al., *Appl. Environ. Microbiol.*, 52:1183–1189 (1986).
Brisbane et al., *Antimicrob. Agents Chemother.*, 31:1967–1971 (1987).
Gurusiddaiah et al., *Antimicrob. Agents Chemother.*, 29:488–495 (1986).
Gutterson et al., *J. Bacteriol.*, 165:696–703 (1986).
Salcher et al., *J. Gen. Microbiol.*, 118:509–513 (1980).
Kraus et al., *Phytopathology*, 79(8):910, Abstract for (List continued on next page.)

*Primary Examiner*—Douglas W. Robinson
*Assistant Examiner*—Deborah K. Ware
*Attorney, Agent, or Firm*—W. Murray Spruill

[57] ABSTRACT

Purified bacterial strains that are effective for the inhibition of plant pathogens, including the fungi *Rhizoctonia solani* and *Pythium ultimum* have been isolated. These strains are useful as biocontrol agents, and can be used to produce antifungal metabolites, such as antibiotic compounds, active against the plant pathogenic fungi *Rhizoctonia solani* and *Pythium ultimum*. Both the purified bacterial strains and the antibiotic compounds can be used as active agents for biocontrol compositions.

5 Claims, No Drawings

OTHER PUBLICATIONS

Annual Meeting, Pacific Division, The American Phytopathological Society.

Howie et al., *Phytopathology*, 79(10):1160, Abstract 201, 1989 Annual Meeting of the American Phytopathological Society.

Weller et al., Journal of Cellular Biochemistry, Supplement 13A:154, Abstract CB104.

Kroos et al., *PNAS USA*, 81:5816–5820 (1984).

Cook et al., *Soil Biol. Biochem.*, 8:269–273 (1976).

Schroth et al., *Science*, 216: 1376–1381 (1982).

European Search Report.

Brisbane et al., *Soil Biol. Biochem*, 21(8):1019–1026 (1989).

Howell et al., Phytopathology, 69(5):480–482 (1979).

Keel et al., *Symbiosis*, 9(1–3):327–341 (1990).

Lievens et al., *Pesticide Science*, 27(2):141–154 (1989).

Merck Index, 1989, 11th ed., p. 931 #5826.

Biological Control of Soil–Borne Plant Pathogens., Leyns et al 1990, abstract only.

ANTI-PATHOGENIC BACTERIAL STRAINS OF *PSEUDOMONAS FLUORESCENS*

This application is continuation, of application Ser. No. 07/705,424, filed May 24, 1991, now abandoned.

FIELD OF THE INVENTION

The present invention relates to the identification and isolation of novel bacterial strains which are effective biocontrol agents. More specifically, the present invention relates to bacterial strains which have been found to inhibit the growth of fungal plant pathogens. More specifically, the present invention relates to previously unknown strains of bacteria, such as members of the genus Pseudomonas, including members of the species *Pseudomonas fluorescens*, which have been found to produce antifungal metabolites, such as antibiotic compounds, that are effective against fungi, including the plant pathogenic fungi *Rhizoctonia solani* and *Pythium ultimum*.

BACKGROUND OF THE INVENTION

It has been recognized that crops grown in some soils are naturally resistant to certain fungal pathogens. Furthermore, soils that are conducive to the development of these diseases can be rendered suppressive, or resistant, by the addition of small quantities of soil from a suppressive field. Scher et al. *Phytopathology* 70:421 (1980). Conversely, suppressive soils can be made conducive to fungal diseases by autoclaving, indicating that the factors responsible for disease control are biological. Subsequent research has demonstrated that root colonizing bacteria are responsible for this phenomenon known as biological disease control (BDC). Baker et al., *Biological control of plant pathogens,* (Freeman Press, San Francisco) (1974).

In many cases, the most efficient strains of biological disease controlling bacteria are fluorescent pseudomonads. Weller et al., *Phytopathology,* 73:463–469 (1983). These bacteria have also been shown to promote plant growth in the absence of a specific fungal pathogen by the suppression of detrimental rhizosphere microflora present in most soils. Kloepper et al., *Phytopathology* 71:1020–1024 (1981). Important plant pathogens that have been effectively controlled by seed inoculation with these bacteria include *Gaeumannomyces graminis,* the causative agent of take-all in wheat, Cook et al., *Soil Biol. Biochem* 8:269–273 (1976) and *Pythium ultimum* and *Rhizoctonia solani,* pathogens involved in damping off of cotton. Howell et al., *Phytopathology* 69:480–482 (1979). *Rhizoctonia* is a particularly problematic plant pathogen for several reasons. First, it is capable of infecting a wide range of crop plants. Second, there are no commercially available chemical fungicides that are effective in controlling the fungus. Because of these circumstances, an inhibitor against *R. solani* would be of substantial interest as a potential control for this pathogen.

Many biological control Pseudomonas strains produce metabolites, such as antibiotics, that inhibit the growth of fungal pathogens. Howell et al., *Phytopathology* 69:480–482 (1979); Howell et al. *Phytopathology* 70:712–715 (1980). These have been implicated in the control of fungal pathogens in the rhizosphere. Several past studies have focused on the effects of mutations that result in the inability of the disease control bacterium or fungus to synthesize these compounds. Kloepper et al., *Phytopathology* 71: 1020–1024 (1981); Howell et al., *Can. J. Microbiol.* 29:321–324 (1983). In these cases, the ability of the organism to control the disease was all but eliminated. In particular, Howell et al., *Phytopathology* 69:480–482 (1979) discloses a strain of *Pseudomonas fluorescens* which was shown to produce an antibiotic substance that is antagonistic to *Rhizoctonia solani.*

In Baker et al., *Biological Control of Plant Pathogens,* (American Phytopathological Society, St. Paul, Minn.)(1982), pages 61–106, it is reported that an important factor in biological control is the ability of an organism to compete in a given environment. Thus, it is desirable to obtain novel strains of biocontrol agents which effectively control the growth of plant pathogens, particularly fungi, such as *Rhizoctonia solani* and *Pythium ultimum,* and are able to aggressively compete with indigenous bacteria and other microflora that exist in the rhizosphere of the plant.

SUMMARY OF THE INVENTION

Accordingly, it is one object of the present invention to provide effective fungicide treatments for the protection of crops from plant pathogens, particularly fungi, such as *Rhizoctonia solani* and *Pythium ultimum.*

It is another object of the present invention to provide strains of bacteria that can be used to control pathogenic attack on crop plants.

It is one feature of the present invention to provide novel strains of bacteria which are useful in producing antifungal metabolites, such as antibiotic compounds, inhibitory to plant pathogens.

It is one feature of the present invention that novel strains of Pseudomonas are provided that are active against plant pathogens, particularly fungi, including the plant pathogenic fungi *Rhizoctonia solani* and *Pythium ultimum.*

It is one advantage of the present invention that biocontrol agents are provided which are active against the plant pathogenic fungi *Rhizoctonia solani* and *Pythium ultimum.*

According to the present invention, the above objectives are carried out by the isolation and use of novel strains of bacterial biocontrol agents that are active against the plant pathogenic fungi *Rhizoctonia solani* and *Pythium ultimum.* The isolation of such biocontrol agents is important for several reasons. First, *R. solani* is a particularly pernicious plant pathogen. The affected plants include beans, wheat, tomato and potato, in addition to cotton. Second, there are no environmentally safe and effective fungicide treatments available for the protection of crops from *R. solani.* Therefore, the use of the biocontrol agents to control or prevent *R. solani* infections in crop plants by application of a live metabolite or antibiotic-producing bacterium or the antibiotic compound itself, may provide the first environmentally safe and effective method of control of this pathogen. In addition the bacterium can be used to produce commercial amounts of compounds that are effective for control of plant pathogens, such as *R. solani.*

In addition, the biocontrol agents of the present invention can be used in mixtures in conjunction with other bacterial strains that otherwise are not effective biocontrol agents for *R. solani* and *P. ultimum* and thereby increase the effective range of these biocontrol strains. The use of the biocontrol agents of the present invention in mixtures in order to improve the biocontrol capabilities of other strains of rhizosphere biocontrol agents is also part of the present invention.

For example, U.S. Pat. No. 4,456,684, (Weller et al.) discloses that take-all, a disease of wheat caused by the fungus *Gaeumannomyces gramminis,* can be controlled in some cases by the application of bacteria inhibitory to this pathogen to wheat seeds prior to planting. However, where the growth of *G. gramminis* is effectively under control, *R. solani* may become a growing problem pathogen of wheat (J. Cook, personal communication). Thus, the biocontrol agents of the present invention can be used together with biocontrol agents intended to protect wheat from take-all. and extend their range of effectiveness to include *R. solani* and *P. ultimum.*

The bacterial biocontrol agents of the present invention may also be used in combination with chemical compounds, such as chemical fungicides, that are compatible with bacterial strains. Among the preferred chemical fungicides is metalaxyl, which is effective against *Pythium ultimum.*

The bacterial biocontrol agents of the present invention may also be useful to produce substances which may be used as active ingredients in antifungal compositions for application to soil. The substances produced by the biocontrol agents of the present invention may be used in any manner known in the art, including coating seeds with an effective amount of the substance, or in furrow application of the substance directly into the soil. It is also contemplated that the biocontrol agent may itself be used as the active ingredient in compositions prepared so as not to prove fatal to the biocontrol agent.

DETAILED DESCRIPTION OF THE INVENTION

In one embodiment of the present invention, purified biocontrol agents are provided which are able to inhibit the growth of fungal pathogens such as *Rhizoctonia solani* and *Pythium ultimum* . These biocontrol agents are preferably purified bacterial strains, and more preferably gram negative bacterial strains, such as the pseudomonads. Most preferred as the biocontrol agent are strains of the species *Pseudomonas fluorescens.* The present invention may also comprise a mixture of bacterial strains, wherein at least one of the bacterial strains is a purified biocontrol agent. The purified biocontrol agents of the present invention may also be conjugated with other bacterial strains for the transfer of their beneficial antibiotic activity.

The biocontrol agents may be applied in any method known for treatment of seed or soil with bacterial strains. For example, see U.S. Pat. No. 4,863,866. These methods may include soil inoculation, seedling inoculation, and seed coating. Some of the strains may be effective for biocontrol even if the bacterium is not living. For other strains, it is preferable to apply a living bacterium.

Another embodiment of the present invention provides methods of inhibiting the growth of fungal pathogens such as *Rhizoctonia solani* and *Pythium ultimum* . In the methods of the present invention, the purified biocontrol agents can be applied in any manner known in the art to be effective for the inhibition of fungal pathogens, such as *Rhizoctonia solani* and *Pythium ultimum* , resulting in an effective biocontrol strain.

In yet another embodiment of the present invention, methods are provided for obtaining an antifungal metabolite, such as an antibiotic compound, which effectively inhibits the growth of fungal pathogens, such as *Rhizoctonia solani* and *Pythium ultimum* . This method comprises culturing the purified biocontrol agents under conditions sufficient to allow the production of an antifungal metabolite, such as an antibiotic compound, and extracting the metabolite or compound.

The present invention embraces the preparation of antifungal compositions in which one or more of the purified biocontrol bacterial strains are used as active ingredient. The present invention further embraces the preparation of antifungal compositions in which the active ingredient is the antifungal metabolite or antibiotic compound produced by the purified biocontrol bacterial strain of the present invention.

Where the active ingredient is a biocontrol bacterial strain, the biocontrol preparation may be applied in any manner known for seed and soil treatment with bacterial strains. The bacterial strain may be homogeneously mixed with one or more compounds or groups of compounds described herein, provided such compound is compatible with bacterial strains. The present invention also relates to methods of treating plants, which comprise application of the bacterial strain, or antifungal compositions containing the bacterial strain, to plants.

The active ingredient of the present invention may also be an antifungal metabolite, such as an antibiotic compound, produced by the biocontrol agents of the present invention. The present invention also relates to methods of treating plants, which comprise application of the antifungal metabolite, such as an antibiotic compound, or antifungal compositions containing the metabolite, to plants.

Such metabolites are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an agrochemical composition which contains at least one of the antifungal metabolites produced by the bacterial strains of the present invention are leaf application, seed coating and soil application. The number of applications and the rate of application depend on the intensity of infestation by the corresponding pathogen (type of fungus). However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare ("ha", approximately 2.471 acres), preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents for compositions containing the antifungal metabolites produced by the biocontrol bacterial strains of the present invention include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonire; and suitable non-sorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants re nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one $C_8$–$C_{22}$ alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from abut 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

While the present invention is described below with reference to specific embodiments thereof, it will be appreciated that numerous variations, modifications, and embodiments are possible, and accordingly, all such variations, modifications and embodiments are to be regarded as being within the spirit and scope of the present invention.

EXAMPLE 1

Collection of Plant and Soil Samples

Plant and soil samples are collected from active cotton-growing areas in Texas. The plant samples are removed directly from the field approximately three to four weeks after planting. Plant samples are placed in plastic bags and stored in an ice chest until returned to the lab. Soil samples are placed in five-gallon plastic containers with lids and stored at 25° C. Where it is not possible to obtain fresh plant samples, soil from the fields is planted with cotton seed at the lab and incubated in the growth chamber to obtain seedlings for sampling purposes.

EXAMPLE 2

Preliminary Screening of Samples for Antibiotic Activity

Dilution series are made from the root systems and adhering soil of cotton seedlings down to $10^{-7}$, and 1 ml aliquots are mixed with 9 mls of molten agar of the following media: trypticase-soy agar, nutrient agar, potato-dextrose agar, King's medium B agar, and soil extract agar. Washed segments of the seedling root systems are also plated directly onto agar plates.

After a three to four day incubation period the plates are inoculated with *Rhizoctonia solani* infested dry-ground wheat bran or agar plugs of *Pythium ultimum*. The plates are observed periodically for the presence of clear zones in the fungal growth around bacterial colonies. Those colonies showing inhibitory or antibiotic activity are streak-purified and placed in dual culture with the fungal pathogens to confirm their antibiotic activity.

The putative antagonists thus identified are graded on a relative scale as to their antibiotic activity against *R. solani* and *P. ultimum* on nutrient agar (high nutrient) and soil extract agar (low nutrient). Strains demonstrating good inhibitory activity on one or more media are stored in 0.85% saline at 5° C. and in sterile soil cultures to maintain their genetic purity.

EXAMPLE 3

Further Screening of Novel Isolates

Inhibitory strains are examined on the basis of morphological, physiological and antibiotic charactreristics. Those strains found not to be duplicates of other isolates are streaked from saline solution onto nutrient agar plates and incubated for three days. The bacteria are then washed from three plates with 30 mls of sterile water.

Inoculum of *R. solani* is prepared by growing the fungus in moist sterile wheat bran or millet for approximately one to two weeks, air drying the material for several days, then grinding the inoculum to 20 mesh with a Wiley mill.

Inoculum of *P. ultimum* is prepared by growing the fungus on sterile moist millet seed for one week. The material is then air-dried and broken up into individual seeds. Alternatively, inoculum of *P. ultimum* may be grown in still liquid cultures of cholesterol-V8 juice medium for approximately 10 days. The mycelial mats are washed and macerated in a waring blender to obtain only oospores.

A suspension of propagules may be mixed into soil at the rate of 2,000 oospores per gram of soil, and the soil incubated for approximately 6 weeks before use, in order to overcome the dormancy factor associated with fresh oospores.

Soil used in the tests for biocontrol efficacy is Lufkin Fine Sandy Loam with a pH of 5.7. The soil is passed through a ¼ inch screen and adjusted to a 15% moisture level. The soil is infested with the pathogens by mixing inoculum and soil together in a cement mixer for 20 minutes at the rate of approximately 0.15 to 0.4 gms of inoculum/13.6 kg of soil for *R. solani* and 20.4 gms of inoculum/13.6 kg of soil for *P. ultimum*. This material may optimally be used for approximately 3 weeks before preparing fresh material.

Infested soil is placed in 20 oz. plastic drinking cups containing 2"×10" cotton cheesecloth wicks passed through a ⅜" hole in the bottom. The wick extends to the soil surface. Five holes 2 cm deep are poked into the soil surface in each cup around the wick, and a seed of the cotton variety Stoneville 213 is placed in each hole.

Alternatively, soil infested with *R. solani* is placed in flats containing about 13.6 kg of soil and partitioned into four sections. Four rows of ten seed each are planted in each section, each seed is treated with about 0.5 ml of bacterial suspension on the seed and about 0.5 ml on the soil surface and the flats are incubated at 25° C. with a 12 hour photoperiod for approximately 14 days. Each section is watered with approximately 250 ml of deionized water every other day. At the end of that period, counts are made of emerged and surviving seedlings.

Soil infested with *P. ultimum* oospores may be placed in 5 gm lots into test tubes containing about 0.75 ml of water or bacterial suspension, and one cotton seed is planted into the center of each. Ten tubes are treated with each bacterial strain, and the tubes are incubated at about 15° C. in the dark for about 7 days. The tubes are then moved to 25° C. and a 12 hour photoperiod for about 3 to 5 days. Counts are made of emerged and surviving seedlings. Bacterial strains whose treatment results in 50% or better seedling survival as an average of three tests are stored in 0.375 ml nutrient broth and 0.125 ml glycerol at −70° C. Cultures of these strains, identified to species, are subjected to further testing.

Treatment of the seed and soil consists of placing 0.5 ml of bacterial suspension from the selected strains on each seed, covering the seed with infested soil, then dispersing 3 ml of bacterial suspension over the entire soil surface in the cup. The soil surface is then sprayed lightly with water, and the cup is covered with a single layer of 0.5 ml plastic wrap and secured with a rubber band. Controls are treated with water.

Treated and control cups are placed in a growth chamber with a 20° C. 12 hr photoperiod and a 16° C. dark period. After approximately four days without supplementary water, the plastic wrap is removed and the wick is placed in a water reservoir 2.5 inches below the cup bottom. After a further six-day incubation, counts are made of emerged and surviving seedlings. Survivors are removed from the soil and examined for evidence of disease or phytotoxic effects on the hypocotyl and root system.

Those strains whose treatment results in 65% or more healthy seedlings are retained, and identified where possible by species according to the morphological and physiological descriptions provided in *Bergey's Manual of Determinative Bacteriology* as well as with the use of identifying tests, such as Rapid NFT (from API Analytab Products). This test measures a number of key biochemical traits that are used to classify the bacteria. This particular kit is designed to distinguish Gram negative, oxidase positive, bacteria, of which, Pseudomonas is one.

EXAMPLE 4

Identification of Effective Biocontrol Strains a. Samples in a given area are taken on the basis of different soil types, different cotton varieties grown, and variations in previous cropping history. Samples are ideally taken when the cotton plant is at the seedling stage, but can be taken at a later stage.

In the first screening, 22 plant and soil samples from five different growing areas are obtained. From dilution assay plates made from these samples in accordance with Example 2. A total of 114 bacteria and 20 actinomycetes are isolated which produce compounds active against *R. solani* or *P. ultimum*.

Of the total numbers of bacteria, 103 strains are active against *R. solani* on nutrient agar, while 59 strains are active on soil extract agar. Of the latter group, eight are also active against *R. solani* on soil extract agar, but not on nutrient agar. This indicates that approximately 50% of the total number of isolated bacterial strains are active only on nutrient agar, while the other 50% are active on both media.

Of those isolates showing activity against *P. ultimum*, 79 are active on nutrient agar and 53 on soil extract agar. Within these two groups 39 are active only on nutrient agar, nine are active only on soil extract agar, and 84 are active on both media.

b. In a second screening, a total of 135 isolates are taken from the sample dilution plates and tested in vitro for activity against *R. solani* and *P. ultimum*. Of these, 35 are active against both pathogens.

A total of 230 strains are assayed in the growth chamber for efficacy as biocontrol agents of Pythium or Rhizoctonia induced damping-off of cotton seedlings. Of these isolates, 29 give better than 65% seedling survival in *R. solani* infested soil, and 12 give better than 65% survival in *P. ultimum* infested soil. A number of these strains are deemed to be duplicates of one another on the basis of antibiotic and biocontrol tests and other physiological characterization. Six selected pseudomonad strains are advanced for further study, along with 10 antibiotic producing actinomycetes. All pseudomonad strains are identified as belonging to *Pseudomonas fluorescens*.

c. In a third screening, a total of 359 isolates screened in dilution plates are retained and genetically stabilized for assay in the growth chamber for biocontrol efficacy. 158 of these isolates are fully tested for biocontrol of *Rhizoctonia solani* or *Pythium ultimum*. Of these, 13 demonstrate good biocontrol of seedling disease incited by *R. solani* or *P. ultimum*, or both. These isolates are identified to species, stored under glycerol at −70° C., and advanced for further study.

EXAMPLE 5

Cultivation of Bacteria and Fungi for Screening Assays a. Cultivation of bacteria The bacterial strains are stored in 50% glycerol at −80° C. prior to use. One loop from the stored culture is suspended in 5 mL Luria Broth (LB: 10 g Bacto-Tryptone, Difco; 5 g yeast extract, Oxoid; 0.25 g $MgSO_4H_2O$; 8 g NaCl; and 1L distilled water; pH 7) and shaken at 150 rpm and 25° C. over night. 100 mL LB is inoculated with 1 mL of the preculture and incubated under the same conditions. 10 mL of the last culture are centrifuged (10 min. at 10000 rpm), and the pellet is resuspended in 200 mL saline (0.8% NaCl) giving a concentration of approx. $10^8$ cfu/ml.

For exact determination a dilution series (100 to $10^{-8}$, 20 uL in 180 uL) is prepared in a microtiter plate and drops of 10 uL are spotted onto Luria Agar (LB with 1.5% Bacto-Agar, Difco) with an Eppendorf pipette. The cfu are counted after 24 hrs incubation at 28° C.

b. Cultivation of *Rhizoctonia solani*

*Rhizoctonia solani* is grown on Potato Dextrose Agar (PDA, Difco), pH 5.6 in a petri dish. A 300 mL-Erlenmeyer flask with 25 g millet and 50 mL distilled water each was autoclaved and incubated with one agar plug (5mm diameter) from a PDA culture of *R. solani*. After incubation at 20° C. in the dark for 3 weeks the overgrown millet is air-dried and ground in a Culatti mill (1 mm sieve, 6000 rpm).

c. Cultivation of *Pythium ultimum*

*Pythium ultimum* is grown on Malt Agar (Oxoid), pH 5.6 in a petri dish. One agar plug (6mm diameter) from this culture is transferred to a petri dish with 8 mL oatmeal agar (50 g Oatmeal 3 mL 1.5% cholestrin in ethanol, and 1L distilled water), with a slant surface. Two hrs later 13 mL of sterile distilled water are added, and the plates are incubated for 10 to 14 days in the dark. The mycelium which grow from the agar surface into the water is transferred to a mixer and cut into small pieces. The concentration of oospores is counted in a Thoma chamber and adjusted with distilled water to $2 \times 10^4$/mL.

EXAMPLE 6

Performance of Screening Assays a. Pathosystem *R. solani*—cotton

Plastic pots (280 mL) are filled first with a thick bottom layer (1 cm) of Vermex F and then with a mixture (7:3 v/v) of steamed, but recolonized St. Aubin soil (sieved, 3mm) and Vermex F. Previously surface sterilized cotton seeds (*Gossypium hirsutum*, cv. Delta Pine) are incubated in hand-warm water for 30 min. and seeded 1 to 1.5 cm deep into the soil. mg of millet powder infested with *R. solani* (see 2.1.2) is added to the center of the pot 1 cm below the surface. All pots are watered with 60 mL water each.

Two hours later each pot is drenched with 20 mL of a bacterial suspension ($10^8$ cfu/mL, see 2.1.1) or 20 mL Monceren (1 mg WP25/mL) resp. resulting in approx. $7 \times 10^6$ cfu/mL soil or 20 ppm Monceren resp. All pots are randomized and incubated in a growth chamber set to 23° C. at daytime (14 hrs) and 18° C. at night (10 hrs) and 50% rel. humidity. The soil is kept moist.

The emergence is recorded after 5, 9 and 13 days. After 20 days the disease incidence is evaluated by rating the plant either healthy ("1") or not germinated or diseased (both "0"), if the root or hypocotyl appears brown and rotted. For each pot with 5 seeds the ratings are summarized resulting in a number of "0" (all plants diseased or not germinated), "1", "2", "3", "4" or "5" (all 5 plants healthy). The numbers from 5 pots per treatment are averaged. The biocontrol efficacy of each treatment in an experiment is given in % in comparison to the control with no treatment and no pathogen (NT.NP, defined as 100% biocontrol) and the control with pathogen only (NT.P, defined as 0% biocontrol).

The biocontrol efficacy of six strains tested against *R. solani* in cotton is presented in Table 1. Strains CGA267356 and CGA281836 show a high level of control (80% and 76%, respectively). The other four strains are somewhat less active but nevertheless exhibit excellent biocontrol activity.

b. Pathosystem *P. ultimum*—cotton

Soil and seeds are prepared as described in part a above, and pots are watered with 50 mL distilled water each. After 1 hr. 20 mL of an oospore suspension ($2 \times 10^4$/mL, see 2.1.3) are drenched into the soil (approx. 1400 cfu/cm$^3$). After another two hours 20 mL of a bacterial suspension ($10^8$ cfu/ml, see 2.1.1) or 20 mL of Ridomil (WP25, 1 mg/mL) resp. is added to each pot resulting in approx. $7 \times 10^6$ cfu/cm$^3$ soil or 20 ppm Ridomil resp. The pots are incubated under the same conditions as described above, and emergence and disease incidence are recorded as mentioned earlier (see part a above).

Table 2 shows the biocontrol efficacy of the same strains against *P. ultimum*. Strain CGA266446 proves to be the most effective strain (56% biocontrol). The rest of the strains show lesser beneficial effects (30 to 44% biocontrol).

c. Pathosystem *R. solani*—tomato

Bacteria (120 ml/6 kg) are added to steamed Pro-mix BX in a mechanical tumbler and tumbled for 5 minutes. The bacterized Pro-mix is allowed to stand in loosely covered buckets for three days before the pathogen inoculum (0.02% colonized oat grains) is added. The mixture is then tumbled for five additional minutes and placed in pots. 5 pots are seeded with 10 tomato seeds (cv. Bonny Best) for each treatment. Terraclor (wp 75, 10.3 kg ai/ha) is added as a control treatment without bacterial treatment and is added as a drench immediately after planting. Each treatment is replicated 4 times. The pots are kept in the headhouse for the first 4 days after seeding (~23° C.) and then moved to the greenhouse for the remainder of the trial. After 15 days the number of healthy plants are counted. A treatment with patbogen but with no bacterial control treatment is prepared as a pathogen check treatment.

Table 3 shows the results of trials of four rhizobacterial strains. CGA266446 and CGA267356 significantly reduce the disease. CGA266447 and CGA270294 are somewhat less active but also demonstrate beneficial effects.

d. Pathosystem *R. solani*—cucumber

Soil is prepared by mixing bacterial cells into raw commercial potting soil at the rate of 1 ml of cells at a density of approximately $10^9$ cells/ml per 10 g of soil. Concurrently, powdered *Rhizoctonia solani*-infested ground millet seed is mixed into the soil at a rate of 10 mg/10 g of soil. The soil is loaded into commercial seedling flats, each consisting of 12 small pots 3 cm square that hold approximately 10 g of soil. A single cucumber seed is planted in each of the 12 pots in each seedling flat and three flats are prepared for each treatment. Uninfested controls that have no pathogen or bacteria added to the soil, and infested controls that have pathogen but no bacteria, are included in each experiment. The flats are placed in a growth chamber in which a constant temperature of 28° C. is maintained and are kept moist by watering twice daily from an overhead sprinkler. At 12 days after planting, the number of surviving plants in each treatment is recorded.

Table 4 shows the results of trials of 3 rhizobacteriai strains. CGA267356 and CGA270293 significantly reduce the disease. CGA266447 is less effective.

EXAMPLE 7

Isolation and Efficacy of Antipathogenic Strains a. Strain CGA266446

Strain CGA266446 is identified as belonging to the species *Pseudomonas fluorescens*. This strain is isolated from the rhizosphere of a mature cotton plant in sandy clay loam in Burleson Co., Texas. The previous crop was corn. The strain is active against both *Rhizoctonia solani* and *Pythium ultimum* on nutrient agar but has only low activity on soil extract agar. Treatment of cotton in soil infested with *R. solani* results in 71% disease control (Table 1). Treatment of cotton in soil infested with *P. ultimum* results in 56% disease control (Table 2). Treatment of tomato in soil infested with *R. solani* results in 123% disease control (Table 3).

b. Strain CGA266447

Strain CGA266447 is identified as belonging to the species *Pseudomonas fluorescens*. This strain is isolated from the same area as, and has similar activity to, Strain CGA266446. Treatment of cotton in soil infested with *R. solani* results in 70% disease control (Table 1). Treatment of cotton in soil infested with *P. ultimum* results in 30% disease control (Table 2). Treatment of tomato in soil infested with *R. Solani* results in 54% disease control (Table 3). Treatment of cucumber in soil infested with *R. solani* results in 10% disease control (Table 4).

c. Strain CGA267356

Strain CGA267356 is identified as belonging to the species *Pseudomonas fluorescens*. This strain is isolated from the rhizosphere of a cotton variety "GP3774" in blackland soil from a farm near Aquilla, Hill County, Tex. The previous crop was wheat. The strain is active against *Rhizoctonia solani* on both nutrient agar and soil extract agar. It is active against *Pythium ultimum* on nutrient agar only. Treatment of cotton in soil infested with *R. solani* results in 80% disease control (Table 1). Treatment of cotton in soil infested with *P. ultimum* results in 44% disease control (Table 2). Treatment of tomato in soil infested with *R. solani* results in 131% disease control (Table 3). The strain produces an antibiotic which is effective to treat *R. solani* and *P. ultimum*, which is described in patent application serial number 570,184, filed on Aug. 20, 1990, the specification of which is hereby incorporated by reference. Treatment of cucumber in soil infested with *R. solani* results in 67% disease control (Table 4).

d. Strain CGA270293

Strain CGA270293 is identified as belonging to the species *Pseudomonas fluorescens*. This strain is isolated from the rhizosphere of a cotton variety "Stoneville 213" in Norwood silty loam from the Texas A&M Research Farm, in Brazos County, Tex. The previous crop was cotton. The strain is active against *Rhizoctonia solani* on both nutrient agar and soil extract agar. It is active against *Pythium ultimum* on nutrient agar only. Treatment of cotton in soil infested with *R. solani* results in 68% disease control (Table 1). Treatment of cotton in soil infested with *P. ultimum* results in 33% disease control (Table 2). Treatment of cucumber in soil infested with *R. solani* results in 53% disease control (Table 4).

e. Strain CGA270294

Strain CGA270294 is identified as belonging to *Pseudomonas fluorescens*. This strain was isolated from the rhizosphere of cotton variety "Stoneville 213" in Miles fine sandy loam from Chilicothe, Texas. The previous crop was cotton variety "Paymaster 145." This strain was active against *R. solani* on nutrient agar and soil extract agar, and against *P. ultimum* on nutrient agar. The strain is active against both *R. solani* and *P. ultimum* in infested soil. Treatment of cotton results in 40% disease control in soil infested with *R. solani* (Table 1) and 34% disease control in soil infested with *P. ultimum* (Table 2). Treatment of tomato in soil infested with *R. solani* results in 46% disease control (Table 3).

f. Strain CGA281836

Upon further culturing of a sample of strain CGA266447, it is found that two distinct strains of bacterium are present. The second bacterium, denoted Strain CGA281836, is morphologically distinct from CGA266447 and exhibits good biocontrol activity. CGA281836 is identified as belonging to the species *Pseudomonas fluorescens*. Treatment of cotton in soil infested with *R. solani* results in 76% disease control (Table 1). Treatment of cotton in soil infested with *P. ultimum* results in 39% disease control (Table 2).

EXAMPLE 8

Inhibition of *Rhizoctonia solani*

The active antifungal metabolite can be extracted from the growth medium of bacterial strains that produce inhibitory antibiotics. For example, using strain CGA267356, this is accomplished by extraction of the growth medium with 80% acetone followed by removal of the acetone by evaporation and a second extraction with diethyl ether. The diethyl ether is removed by evaporation and the dried extract is resuspended in a small volume of water. Small aliquots of the antibiotic extract applied to small sterile filter paper discs placed on an agar plate will inhibit the growth of *R. solani*, indicating the presence of the active antibiotic compound. Since the antibiotic is readily extractable with organic solvents, it is likely to have cyclic or aromatic groups in its structure as is common of many antibiotics known to be produced by other pseudomonads.

EXAMPLE 9

Combination of *P. fluorescens* With the Fungicide Metalaxyl to Control Damping-off of Cotton in Soil Infested With *Rhizoctonia solani* and *Pythium ultimum*

Strains 281836, 267356 and 270293 are each applied to non-sterile soil as a drench at $2 \times 10^8$ cfu/ml soil, while metalaxyl fungicide is either drenched (Ridomil, at 0.02, 0.5 or 2 ppm) or coated onto seeds (Apron, at 35 g a.i./100 kg seed). *P. ultimum* is introduced as an oospore suspension (1400 spores/ml soil). *R. solani* is introduced as a pelleted millet powder (5 mg in the center of each pot). After incubation for 19 days in the greenhouse, the hypocotyls of cotton seedlings are rated for disease on an observation scale.

Almost complete control of damping-off is achieved when strain CGA 267356 is applied together with Ridomil at 2 ppm. Using Apron instead of Ridomil results in the same level of control. Strain CGA 267356 alone still gives significant suppression of both pathogens. Metalaxyl fungicide alone fails to control the disease complex.

0.02 ppm Ridomil alone gives 40% suppression of *P. ultimum*. The combination of 0.02 ppm Ridomil with Strain CGA 267356 increases the level of control to more than 60%. Strain CGA 281836 gives results essentially as good as Strain CGA 267356. Strain CGA 270293 does not significantly suppress the seedling disease complex.

The above demonstrates that combined application of biocontrol bacterial strains with a reduced rate of metalaxyl fungicide achieves almost complete control of the seedling disease complex in cotton caused by *R. solani* and *P. ultimum*.

EXAMPLE 10

Formulations of Antifungal Compositions Containing the Antifungal Metabolites Produced by *P. fluorescens* Bacteria Which is Inhibitory to the Growth of *R. solani* as the Active Ingredient In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylohenol polyethylene glycol ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgite | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

EXAMPLE 11

Formulations of Antifungal Compositions Containing the Antifungal Metabolite Produced by *P. fluorescens* Bacteria Which is Inhibitory to the Growth of *R. solani* as the Active Ingredient In the following examples, percentages of compositions are by weight.

| 1. Wettable powders: | a | b | c |
|---|---|---|---|
| Active ingredient | 20% | 60% | 75% |
| Sodium lignosulonate | 5% | 11 5% | — |
| Sodium lauryl sulfate | 3% | — | 5% |
| Sodium diiobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

EXAMPLE 12

Field Trial of Biocontrol Strains

Strains of biocontrol strains are stored in 50% glycerol at −80° C. One loop from the stored culture is suspended in 5 ml Luria Broth (LB: 10 g Bacto-Tryptone, Difco; 5 g yeast extract, Oxold; 0.25 g $MgSO_4x$-$H_2O$; 8 g NaCl; and 1 L distilled water; pH 7) and shaken at 150 rpm and 25° C. for 24 hrs. 100 mL LB is inoculated with 1 mL of the preculture and incubated under the same conditions. After 16 hrs, the culture is centrifuged for 10 minutes at 10,000 rpm, and the pellet is resuspended in saline (0.8% NaCl) and adjusted to 3×109 cfu/ml (OD2). Thus, 100 mL of culture will give approximately 200–300 mL drench of OD2.

A hemocytometer and/or spectrophotometer is used to adjust the concentration of bacteria in the drench. Otherwise, a standard salt solution of a known OD (e.g., Phillips' Milk of Magnesia TM $=Mg(OH)_2$) can be used to adjust the OD of the drench. If a centrifuge is not available, the whole culture broth has to be applied; a hemocytometer is then used to determine the cfu/mL.

For exact determination, a dilution series ($10^{\circ}$ to $10^{-8}$; 20 uL in 180 uL) is prepared in a microtiter plate and drops of 10 uL are spotted onto Luria Agar (LB with 1.5% Bacto-Agar, Difco) with an Eppendorf pipette. The cfu are counted after 24 hrs incubation at 28° C.

250 mL of the bacterial suspension per 10' (=1 rep) are drenched onto the covered seeds (200 seeds per rep). A handheld sprayer or watering can free of pesticide residues is used to apply the drench in a narrow band of approximately 1.5 inches width.

*Rhizoctonia solani* and *Pythium ultimum* are prepared for inoculation as in Example 5 above.

Emergence is recorded at 10 days after planting to assess pre-emegence damping off. Stands are recorded at 21 days and 28 days after planting to assess post-emergence damping-off.

Deposits

The following bacterial strains have been deposited with the American Type Culture Collection, 12301 Parklawn Drive, Rockville, Md. 20852, in accordance with the Budapest Treaty:

CGA 266446 (ATCC Accession No, 55171);
CGA 266447 (ATCC Accession No, 55170);
CGA 267356 (ATCC Accession No, 55169)i;
CGA 270293 (ATCC Accession No, 55175);
CGA 270294 (ATCC Accession No, 55174).; and
CGA 281836 (ATCC Accession No, 55168),

TABLE 1

Biocontrol activity in % of the strains used in the screening against *Rhizoctonia solani* in cotton plants.

| STRAIN | MEAN PERCENT BIOCONTROL ACTIVITY1 |
|---|---|
| CGA266446 | 71 |
| CGA266447 | 70 |
| CGA267356 | 80 |
| CGA270293 | 68 |
| CGA270294 | 40 |

TABLE 1-continued

Biocontrol activity in % of the strains used in the screening against *Rhizoctonia solani* in cotton plants.

| STRAIN | MEAN PERCENT BIOCONTROL ACTIVITY1 |
|---|---|
| CGA281836 | 76 |

1 = Uninfested control designated 100% biocontrol
Infested control designated 0% biocontrol

TABLE 2

Biocontrol activity in % of the strains used in the screening against *Pythium ultimum* in cotton plants.

| STRAIN | MEAN PERCENT BIOCONTROL ACTIVITY1 |
|---|---|
| CGA266446 | 56 |
| CGA266447 | 30 |
| CGA267356 | 44 |
| CGA270293 | 33 |
| CGA270294 | 34 |
| CGA281836 | 39 |

1 = Uninfested control designated 100% biocontrol
Infested control designated 0% biocontrol

TABLE 3

Biocontrol activity in % of the strains used in the screening against *Rhizoctonia solani* in tomato plants.

| TREATMENT | STAND 15 DAP[a] | | | | | % BIOCONTROL ACTIVITY[1] |
|---|---|---|---|---|---|---|
| | REP1 | REP2 | REP3 | REP4 | MEAN | |
| NP.NT[b] | 9 | 10 | 5 | 10 | 8.50 | 100 |
| P.NT[c] | 5 | 4 | 6 | 6 | 5.25 | 0 |
| Terraclor | 10 | 10 | 9 | 10 | 9.75 | 138 |
| CGA266446 | 9 | 9 | 10 | 9 | 9.25 | 123 |
| CGA266447 | 7 | 5 | 6 | 10 | 7.00 | 54 |
| CGA267356 | 9 | 10 | 10 | 9 | 9.50 | 131 |
| CGA270294 | 7 | 6 | 7 | 7 | 6.75 | 46 |

[a] 32 Days After Planting
[b] 32 No Pathogen, No Treatment (Uninfested control)
[c] 32 Pathogen, No Treatment (Infested control)
[1] 32 Uninfested control designated 100% biocontrol
Infested control designated 0% biocontrol

TABLE 4

Biocontrol activity of the strains used in the screening against *Rhizoctonia solani* in cucumber plants.

| TREATMENT | STAND 15 DAP[a] | | | | % BIOCONTROL ACTIVITY[1] |
|---|---|---|---|---|---|
| | REP1 | REP2 | REP3 | MEAN | |
| NP.NT[b] | 12 | 11 | 12 | 11.67 | 100 |
| P.NT[c] | 7 | 10 | 9 | 8.67 | 0 |
| CGA266447 | 9 | 9 | 9 | 9.00 | 10 |
| CGA267356 | 10 | 11 | 11 | 10.67 | 67 |
| CGA270293 | 9 | 11 | 11 | 10.33 | 53 |

[a] 32 Days After Planting
[b] 32 No Pathogen, No Treatment (Uninfested control)
[c] 32 Pathogen, No Treatment (Infested control)
[1] 32 Uninfested control designated 100% biocontrol
Infested control designated 0% biocontrol

What is claimed is:

1. A biologically pure strain of *Pseudomonas fluorescens* selected from ATCC 55171, ATCC 55170, ATCC 55169, ATCC 55175, ATCC 55174. and ATCC 55168.

2. A biocontrol composition comprising at least 0. 1% of at least one *Pseudomonas fluorescens* strain selected from the group consisting of ATCC 55171, ATCC 55170 ATCC 55169, ATCC 5175, ATCC 55174, and ATCC 55168.

3. The biocontrol composition of claim 2, wherein said composition further comprises a chemical fungicide.

4. The biologically pure biocontrol agent according to claim 1, wherein the biocontrol agent effectively inhibits the growth of a fungal pathogen selected from the group consisting of *Rhizoctonia solani* and *Pythium ultimum*.

5. A biocontrol agent according to claim 3, wherein the chemical fungicide is a metalaxyl compound.

* * * * *